United States Patent
Reicher et al.

(10) Patent No.: US 10,600,511 B2
(45) Date of Patent: Mar. 24, 2020

(54) ACCELERATING HUMAN UNDERSTANDING OF MEDICAL IMAGES BY DYNAMIC IMAGE ALTERATION

(71) Applicant: INTERNATIONAL BUSINESS MACHINES CORPORATION, Armonk, NY (US)

(72) Inventors: Murray A. Reicher, Rancho Santa Fe, CA (US); Marwan Sati, Missisauga (CA)

(73) Assignee: International Business Machine Corporation, Armonk, NY (US)

( * ) Notice: Subject to any disclaimer, the term of this patent is extended or adjusted under 35 U.S.C. 154(b) by 193 days.

(21) Appl. No.: 15/900,057

(22) Filed: Feb. 20, 2018

(65) Prior Publication Data
US 2019/0259492 A1  Aug. 22, 2019

(51) Int. Cl.
*G16H 30/40* (2018.01)
*G06N 3/08* (2006.01)
*G06N 3/04* (2006.01)
*G06T 11/60* (2006.01)
*G06T 7/00* (2017.01)

(52) U.S. Cl.
CPC .......... *G16H 30/40* (2018.01); *G06N 3/0427* (2013.01); *G06N 3/084* (2013.01); *G06T 7/0014* (2013.01); *G06T 11/60* (2013.01); *G06T 2207/30004* (2013.01); *G06T 2210/41* (2013.01)

(58) Field of Classification Search
CPC .................. G06T 2207/30004; G16H 30/40
See application file for complete search history.

(56) References Cited

U.S. PATENT DOCUMENTS

| | | | |
|---|---|---|---|
| 6,891,920 B1 * | 5/2005 | Minyard | A61B 6/469 378/37 |
| 7,773,097 B2 * | 8/2010 | Merzenich | G09B 19/00 345/619 |

(Continued)

FOREIGN PATENT DOCUMENTS

| | | |
|---|---|---|
| CN | 107145910 A | 9/2017 |
| CN | 107358038 A | 11/2017 |

(Continued)

OTHER PUBLICATIONS

Lee et al., "Fully Automated Deep Learning System for Bone Age Assessment," Journal of Digital Imaging, 2017, 15 Pages, vol. 30, Issue 4, Springer International Publishing.

(Continued)

*Primary Examiner* — Gandhi Thirugnanam
(74) *Attorney, Agent, or Firm* — Reza Sarbakhsh

(57) ABSTRACT

A method, computer system, and a computer program product for dynamically altering at least one image is provided. The present invention may include receiving a plurality of data, wherein the received plurality of data includes at least one existing medical image. The present invention may also include determining that one or more user instructions for the received existing image were received. The present invention may then include implementing the one or more user instructions on the received existing medical image. The present invention may also include altering the received existing medical image based on the one or more implemented user instructions and a medical knowledge base.

19 Claims, 5 Drawing Sheets

(56) References Cited

U.S. PATENT DOCUMENTS

| | | | |
|---|---|---|---|
| 9,256,962 B2* | 2/2016 | Berry | G06T 19/006 |
| 2003/0018457 A1* | 1/2003 | Lett | G06T 5/002 |
| | | | 703/11 |
| 2003/0065523 A1* | 4/2003 | Pruche | A45D 44/005 |
| | | | 382/118 |
| 2003/0144976 A1* | 7/2003 | Brady | G06F 19/324 |
| | | | 706/46 |
| 2003/0229278 A1* | 12/2003 | Sinha | G06K 9/6247 |
| | | | 600/407 |
| 2006/0105825 A1* | 5/2006 | Findlay | A63F 13/12 |
| | | | 463/4 |
| 2007/0166675 A1* | 7/2007 | Atkins | G09B 5/06 |
| | | | 434/236 |
| 2007/0196803 A1* | 8/2007 | Goodrich | G09B 5/00 |
| | | | 434/323 |
| 2008/0132781 A1* | 6/2008 | Redel | A61B 5/02014 |
| | | | 600/419 |
| 2008/0187896 A1* | 8/2008 | Savitsky | G09B 23/28 |
| | | | 434/272 |
| 2008/0247620 A1* | 10/2008 | Lewis | G06T 19/006 |
| | | | 382/128 |
| 2009/0268952 A1* | 10/2009 | Schaffer | G06K 9/6217 |
| | | | 382/128 |
| 2011/0159470 A1* | 6/2011 | Hradek | G09B 23/28 |
| | | | 434/262 |
| 2011/0236868 A1* | 9/2011 | Bronstein | G09B 23/30 |
| | | | 434/267 |
| 2012/0197619 A1* | 8/2012 | Namer Yelin | G16H 50/50 |
| | | | 703/11 |
| 2013/0006087 A1* | 1/2013 | Kondo | G06O 50/22 |
| | | | 600/407 |
| 2014/0365232 A1* | 12/2014 | Sadeghi | G16H 50/20 |
| | | | 705/2 |
| 2015/0112701 A1* | 4/2015 | Julian | G06Q 50/22 |
| | | | 705/2 |
| 2015/0363053 A1* | 12/2015 | Aoyama | G06F 3/0482 |
| | | | 715/838 |
| 2016/0350919 A1* | 12/2016 | Steigauf | G06T 7/0014 |
| 2017/0116498 A1* | 4/2017 | Raveane | G06N 3/10 |
| 2019/0259492 A1* | 8/2019 | Reicher | G06T 7/0014 |

FOREIGN PATENT DOCUMENTS

| | | |
|---|---|---|
| CN | 107688815 A | 2/2018 |
| WO | 2017182369 A1 | 10/2017 |
| WO | 2019162789 A1 | 8/2019 |

OTHER PUBLICATIONS

Mell et al., "The NIST Definition of Cloud Computing," National Institute of Standards and Technology, Sep. 2011, p. 1-3, Special Publication 800-145.

Zhang et al., "MDNet: A Semantically and Visually Interpretable Medical Image Diagnosis Network," IEEE Conference on Computer Vision and Pattern Recognition, 2017, p. 3549-3557, IEEE Computer Society.

International Search Report and Written Opinion, International Application No. PCT/IB2019/050999, International Filing Date: Feb. 7, 2019, dated Jun. 12, 2019, 9 pages.

* cited by examiner

ACCELERATING HUMAN UNDERSTANDING OF MEDICAL IMAGES BY DYNAMIC IMAGE ALTERATION

BACKGROUND

The present invention relates generally to the field of computing, and more particularly to cognitive computing.

The development of expertise utilizes a series of events: demonstration, imitation with correction, and repetition. Ultimately, an expert acquires gestalt (i.e., the ability to rapidly recognize normality and abnormality via a global appreciation of visual input). As a result, the expert processes visual input (i.e., images), including the recognition of salient imaging finding differently than less-skilled individuals.

The development of intuitive recognition of images typically requires years of training, and is often referred to as the development of gestalt. Training provides frequent close-loop feedback in which abnormalities and normalities may be understood in relation to either a comparable image or mental expectation.

SUMMARY

Embodiments of the present invention disclose a method, computer system, and a computer program product for dynamically altering at least one image based on the system having an underlying understanding of the imaging manifestations of one or more diseases and receiving user instruction as either user input or acting on stored image presentation rules (i.e., configurable rules or previously determined user rules). The present invention may include receiving a plurality of data, wherein the received plurality of data includes at least one existing medical image. The present invention may also include determining that one or more user instructions for the received existing image were received. The present invention may then include implementing the one or more user instructions on the received existing medical image. The present invention may also include altering the received existing medical image based on the one or more implemented user instructions and a medical knowledge base.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
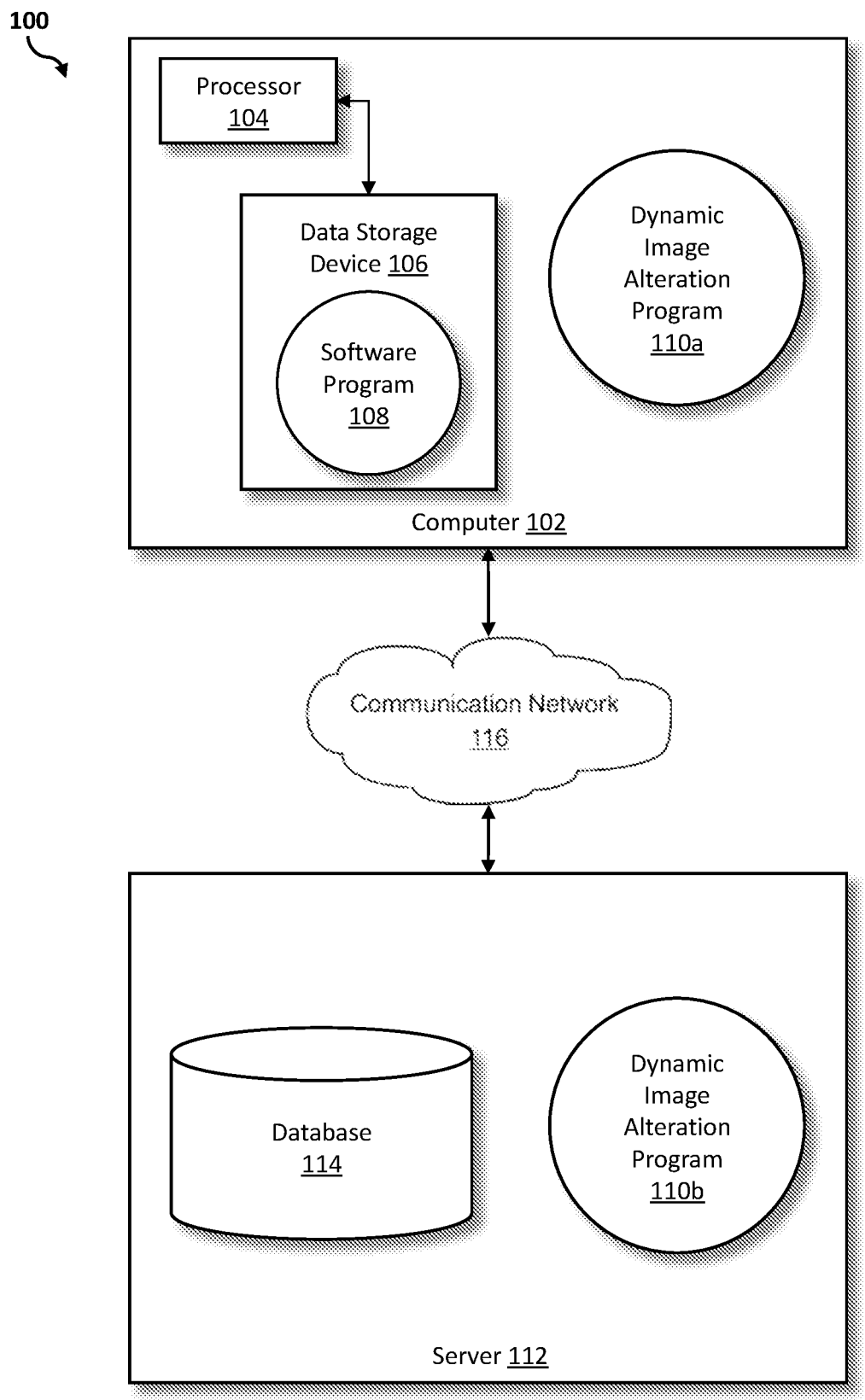
FIG. 1 illustrates a networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language, Python programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for dynamically altering at least one image. As such, the present embodiment has the capacity to improve the technical field of cognitive computing by dynamically altering images based on user interaction (i.e., user rules and/or user input). More specifically, the dynamic image alteration program may receive data (i.e., textual and visual data) associated with a specific patient. The dynamic image alteration program may then display the existing images associated with the patient to the user. If the dynamic image alteration program determines that the user previously provided rules, then the dynamic image alteration program may apply these previously determined user rules (i.e., configurable rules) and then proceed to determine whether user input existed and apply existing user input. If, however, the dynamic image alteration program failed to provide any user rules, then the dynamic image alteration program may proceed to apply user input. The dynamic image alteration program may then retrieve images from a deep learning (e.g., generative adversarial network) and image analysis engine with a medical knowledge base and may generate at least one altered image based on the previously determined user rules and/or user input. The dynamic image alteration program may then determine whether the user has additional user input, which may be utilized to generate additional altered images (i.e., secondary altered images).

As described previously, the development of expertise utilizes a series of events: demonstration, imitation with correction, and repetition. Ultimately, an expert acquires gestalt (i.e., the ability to rapidly recognize normality and abnormality via a global appreciation of visual input). As a result, the expert processes visual input (i.e., images), including the recognition of salient imaging finding differently than less-skilled individuals.

The development of intuitive recognition of images typically requires years of training, and is often referred to as the development of gestalt. Training provides frequent closeloop feedback in which abnormalities and normalities may be understood in relation to either a comparable image or mental expectation.

Machine learning algorithms may create images through generative adversarial networks. A large amount of data may be gathered and the model may be trained to generate similar data. The neural networks utilized in generative models may have significantly fewer parameters than the generative model that the data may be trained on. As such, the generative models may discover and generate the critical portions of the data.

Therefore, it may be advantageous to, among other things, utilize deep learning and image analytics to generate abnormalities on images in response to user input or rules, especially in the healthcare field. In the healthcare field of medical imaging, training doctors typically takes several years, and even seasoned professionals require ongoing training. Therefore, a system that can accelerate the development of gestalt expertise may accelerate and improve training, as well as be useful in daily practice to assist medical personnel and medical professionals to recognize imaging manifestations of disease and normal conditions.

In the present embodiment, the dynamic image alteration program may utilize deep learning and image analytics to generate abnormalities on images in response to user input or rules. Deep learning is a subfield of machine learning associated with known algorithms, inspired by the structure and function of the neural network in the animal visual cortex. Deep learning may utilize a neural network to classify or cluster images. As deep learning is utilized more frequently to assess images, computerized systems that analyze the images may learn to receive features and findings that depict various abnormalities (e.g., diseases, mutations). In addition to analyzing the images, the computerized systems may modify the images to depict specific normal and abnormal findings. For example, a radiologist may examine thousands of chest radiographs in teaching files or actual practice in order to develop an understanding of the various manifestations of congestive heart failure. Over time, the radiologist may develop the ability to diagnose congestive heart failure on radiographs by gestalt. The same radiologist may similarly review thousands of radiographs to understand the appearances of pulmonary edema. After the review of several thousand examples, the radiologist may learn how to differentiate pulmonary edema from other causes of thickened lung interstitial tissues. As such, a physician in training or in-practice may benefit from a computerized display of a spectrum of diseases or other anatomical variations. In some cases, these abnormalities may be dynamically created on images of a particular patient that is the subject of an imaging examination.

According to at least one embodiment, the dynamic image alteration program may utilize artificial intelligence and a knowledge base with a computerizing medical image display program (e.g., picture archiving and communication system (PACS), a medical imaging technology that provides economical storage and convenient access to images from multiple modalities) to present images that may be controlled by the user, and are based on real (i.e., existing) and generated images. In the dynamic image alteration program, the same images may be dynamically modified to display an increase or decrease in the severity of one or multiple diseases, a progression or regression of one or multiple diseases, the disease flipped from left to right side, or a continuation of certain activities (e.g., risky behaviors or habits) by an individual. The dynamic image alteration program may include the modification of an image to show different disease states providing the comparison of each image side-by-side, or via alternative comparative display means (e.g., viewing the images on different image viewers), or displaying a movie-like dynamic alteration of an image. The dynamic image alteration program may utilize automated rules to control the display of created images and their arrangement relative to the existing images of the specific patient. The automated rules may be responsive to the user, exam indications, patient demographics, location and site configuration. The dynamic image alteration program may also retrieve, generate or display images of other body regions to show the user other manifestations of systemic diseases that may affect multiple organs.

The present embodiment may be integrated into another program to generate differential diagnosis to automatically show the most likely symptoms and effects of various diseases in the differential diagnosis.

The present embodiment may be utilized to create new anatomical findings. The dynamic image alteration program may be triggered by previously determined user rules, user input or both (i.e., user interaction) to generate an image with an altered anatomy. According to at least one embodiment, the dynamic image alteration program may alter a portion of an image based on user interaction (i.e., user rules and/or user input).

According to at least one embodiment, the dynamic image alteration program may understand the features and findings of various related diseases on chest radiographs, including various different views (e.g., posteroanterior (PA), anteroposterior (AP), lateral, supine, upright and decubitus view) in patients of various age, gender, race, and stature, and the dynamic image alteration program may produce a spectrum of findings in response to user input or programmed rules. For example, a radiologist using a PACS may start with a normal chest upright PA chest radiograph and slowly dial-in early congestive heart failure, moderate, or severe congestive heart failure with pulmonary edema, then non-cardiogenic pulmonary edema of various causes, then interstitial lung disease of various causes. In a short period of time, the physician may observe, with real-time feedback, a spectrum of cognitive experiences that may otherwise take years to obtain and compare. This process may be repeated with supine chest radiographs, AP vs. PA views, young patients, or old patients. As such, years of training may be compressed into minutes or hours.

According to at least one embodiment, the dynamic image alteration program may include the dynamic modification of at least one image based on the specific imaging exam or group of exams as driven by a user input or rule, or various information associated with the exam or patient. Such dynamic displays may increase both the specificity and sensitivity of detecting and distinguishing various abnormalities and may accelerate the development of user experience and the intuitive decision making of the user (e.g., gestalt). For example, a radiologist or other clinical expert may be provided a chest radiograph with a history of possible sarcoidosis. The dynamic image alteration program may not only display the image, but the dynamic image alteration program may also show what sarcoidosis may look like on this particular image. The dynamic image alteration program may enable the user to display various manifestations and stages of the disease, and the dynamic image alteration program may show what the exam would look like if automatically detected or manually specified abnormalities were removed. In the present embodiment, the dynamic image alternation program may continue to train the user with generative images until the user achieves a certain level of sensitivity and specificity.

According to at least one embodiment, the dynamic image alteration program may create a series of altered images showing the manifestations, stages and severity of an abnormality, or display altered images on the effect of the abnormality. Such altered images may assist an expert to detect abnormalities, and the various manifestations resulting from the abnormalities, as well as the effects of the abnormalities. For example, in the case of sarcoidosis, the dynamic image alteration program may visually show skeletal or cerebral manifestations that may result from the disease, or how the disease in the chest may appear when it progresses or regresses. The dynamic image alteration program may also show other manifestations of the disease in other organs.

According to at least one embodiment, the dynamic image alteration program may be utilized to assist non-specialists by displaying comparable images to the user. The user may request that the dynamic image alteration program generate multiple images for comparison. As such, the user may compare images in whole or part with another image from the same or another source, or a stored image or non-visual representation. For example, the dynamic image alteration program or associated program may use data from the patient's medical record and provide a differential diagnosis, then the dynamic image alteration program may alter the images to show how various diagnostic possibilities might be manifested on the particular images being viewed. In another example, the dynamic image alteration program may identify a finding on a skeletal radiograph that may indicate the differential diagnosis includes non-displaced fracture, nutrient vessel canal, or artifact. Using the dynamic image alteration program, the user may alter the image to show a typical non-displaced fracture, a typical nutrient canal, or examples of common artifacts that may masquerade as such pathology to help the user appreciate which of the diagnostic possibilities comes closest to the current appearance. The dynamic image alteration program may alter the images currently being viewed to supply a reference standard for optimal comparison.

According to at least one embodiment, the dynamic image alteration program may be utilized for individual education or behavior modification. The user may generate comparable images in an attempt to modify the behavior of another individual (e.g., patient). For example, a patient who is a smoker may have a chest radiograph showing minimal abnormalities. Utilizing the dynamic image alteration program, the patient, who is a smoker, may be shown the progression of disease that may be expected if the patient continues to smoke.

The present embodiment may be utilized in various fields, such as medical imaging, and non-static images (e.g., video or movies). According to at least one embodiment, the dynamic image alteration program may be utilized by the user to develop the skill of rapidly responding to images in various professions (e.g., pilots, fire fighters, police officers, physicians, drivers). For example, by dynamically altering images of a normal body part, the dynamic image alteration program may help train a doctor to recognize the earliest manifestations of a disease, not just the later stages when the manifestations are more obvious. Similarly, the dynamic image alteration program may be used to train a fighter pilot or professional quarterback (i.e., American football player).

The present embodiment may include a database to store and index images based on the user preferences in a specific domain. For example, in the field of medical imaging, a database of medical images with known disease types may be established and indexed with patient demographics (e.g., age, height, weight, sex, ethnicity), image modality (x-ray, MRI, ultrasound) and orientation for two dimensional images (e.g., AP x-ray, lateral x-ray) or for cross-sectional images (e.g., axial, coronal, sagittal). The images with specific disease types may be organized into demographic groups, such as Caucasian females aged 50-55 with Hepatocellular Carcinoma (HCC). As such, the user may open a medical image for viewing and may select a specific disease type, or if in training mode, the dynamic image alteration program may select a disease type. According to at least one embodiment, for training or research purposes, the dynamic image alteration program may determine the patient demographic, image type and laterality through information in the hospital electronic medical record and information with the image header (e.g., digital imaging and communications in medicine (DICOM) header) related to the existing images. The generated information may be utilized to identify existing images within the current patient's demographic, and an altered image depicting the disease corresponding to the existing images may be established.

According to at least one embodiment, the dynamic image alteration program may register the altered images to a current individual or circumstance. The dynamic image alteration program may compute an image registration, for example, by solving a non-convex, non-linear optimization problem balancing two competing forces: (1) the similarity of fixed and warped images (e.g., mutual information); and (2) the smoothness or invertibility of the vector deformation field. Once registered, the user may modify the blending or comparison between the current images and the abnormal images by viewing the images side-by-side, or alternatively by toggling or shuffling back and forth between the images.

According to at least one embodiment, the dynamic image alteration program may alternate between the discriminator and generator for training purposes (i.e., generative adversarial networks). The generator parameter weights may be fixed to train the discriminator to distinguish between real and generated images. The error between the real and generated images may be the loss that is fed back (i.e., back propagated) to update the discriminator weights. The discriminator parameter weights may be fixed as the generator creates samples. The error may be fed back to update the generator weights. Both the generator parameter weights and discriminator parameter weights may be iterated until convergence. A successful result may be based on whether the discriminator is unable to distinguish the difference between the real and generated images created by the generator (e.g., Turing test).

According to at least one embodiment, in the medical imaging field, the dynamic image alteration program may apply deep learning to medical images to determine features that depict anatomy. The dynamic image alteration program may then review medical literature about diseases in a deep learning neural network. The dynamic image alteration program may then index data about the various disease states and diseased image features. The dynamic image alteration program may then obtain a new exam. The dynamic image alteration program may then match the exam images to similar anatomy with the specified disease based on the user rule or input. The dynamic image alteration program may then register and deform to alter the existing image to match the features of a particular disease. The dynamic image alteration program may then enable the user to input the severity of the disease.

According to at least one embodiment, in the medical imaging field, the dynamic image alteration program may apply deep learning or other artificial intelligence to medical images to determine features that depict anatomy. The dynamic image alteration program may then review medical literature about diseases in a deep learning neural network. The dynamic image alteration program may then index data about the various disease states and diseased image features. The dynamic image alteration program may then obtain a new exam. During a pre-reading or reading process, the dynamic image alteration program may then generate images to show various manifestations and stages of one or more diseases per user rule or input by altering an existing image. The dynamic image alteration program may then provide a user input or configurable rules for the user to display various images, which may include an option to store rules to determine when and how these modified images are automatically displayed, or generate a search or input process (e.g., extracting information about the reason for the exam or patient's differential diagnosis) to determine which images are displayed.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and a dynamic image alteration program 110a. The networked computer environment 100 may also include a server 112 that is enabled to run a dynamic image alteration program 110b that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 3, server computer 112 may include internal components 902a and external components 904a, respectively, and client computer 102 may include internal components 902b and external components 904b, respectively. Server computer 112 may also operate in a cloud computing service model, such as Software as a Service (SaaS), Analytics as a Service (AaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the dynamic image alteration program 110a, 110b may interact with a database 114 that may be embedded in various storage devices, such as, but not limited to a computer/mobile device 102, a networked server 112, or a cloud storage service.

According to the present embodiment, a user using a client computer 102 or a server computer 112 may use the dynamic image alteration program 110a, 110b (respectively) to dynamically alter an image based on user rules and actions. The dynamic image alteration method is explained in more detail below with respect to FIG. 2.

Figure 2:
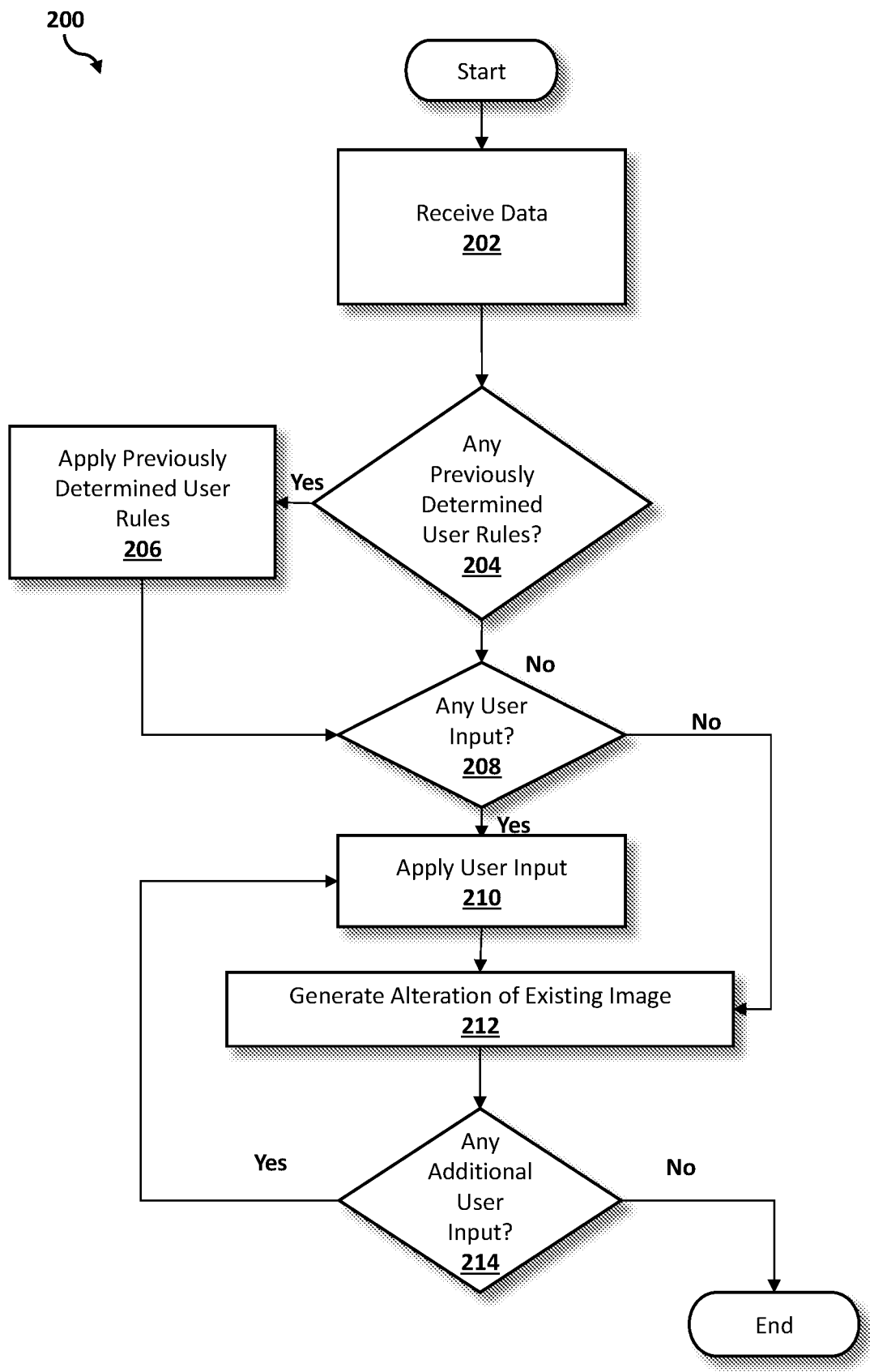
FIG. 2 is an operational flowchart illustrating a process for dynamically altering images based on user instruction (i.e., previously determined user rules and/or user input) according to at least one embodiment.

Referring now to FIG. 2, an operational flowchart illustrating the exemplary image alteration process 200 used by the dynamic image alteration program 110a and 110b according to at least one embodiment is depicted.

At 202, data is received by the dynamic image alteration program 110a, 110b. Using a software program 108 on the user's device (e.g., user's computer 102), data may be received as input from a known computerized medical image display program (e.g., picture archiving and communication system (PACS), which provides economical storage and convenient access to images from multiple modalities) to the dynamic image alteration program 110a, 110b via communications network 116. The data may include visual data (e.g., x-rays, scans, graphs), and textual data (e.g., medical records without images) associated with a patient. The textual data may be utilized to identify the images (i.e., existing images) located in the received data, or to extract assertions or connections between the existing images. Alternatively, the user may also manually input visual and textual data into the dynamic image alteration program 110a, 110b, without the use of a computerized medical image display program.

For example, a patient, a 39-year-old female, was diagnosed with anaplastic astrocytoma (i.e., a grade III brain tumor that develops from star-shaped astrocytes that support nerve cells) in the right cerebral hemisphere. A radiation oncology resident (i.e., resident), with very limited experience with brain tumor cases, is assisting a team of physicians, which includes neurosurgeons, oncologists and a senior radiation oncologist, to treat the patient. As such, the resident utilizes the dynamic image alteration program 110a, 110b to gain more experience on the progression and stages of anaplastic astrocytoma. The resident obtains the patient's medical records including computed tomography scans (CT scans), magnetic resonance imaging scans (MRI scans), x-rays, physician notes and reports from a PACS, and uploads the patient's medical records, via an encrypted virtual server, into the dynamic image alteration program 110a, 110b.

In the present embodiment, the existing images may be displayed by the computerized medical image display program. Using the data received from 202, the computerized medical image display program may display the existing images received before determining the user instruction (i.e., configurable rules/previously determined user rules and/or user input) that may be applied (i.e., implemented) on the existing images. The user, for example, may view existing images, such as CT and MRI scans, utilizing the computerized medical image display image program, prior to creating alterations to the existing image.

Then, at 204, the dynamic image alteration program 110a, 110b determines if there are previously determined user rules. Before the user receives data at 202, the user may provide rules to the dynamic image alteration program 110a, 110b. At the bottom of the screen, there is a "User Rules" button displayed. Once the user clicks on the "User Rules" button, the user may be prompted (e.g., via a dialog box) to include rules to alter (i.e., anatomically alter or change) the existing image. The dialog box may include a list of categories for the user rules (e.g., age group, medical field, body part, orientation). To the left of each category, there may be a box for the user to click to select that category. To the right of the category, there may be a box for the user to provide additional information associated with the specific category (e.g., if the user clicks age group, the user may determine which age groups may be included or excluded, or for a medical field, the user may determine which medical fields may be included or excluded). Under the list of categories, there may be a box for the user to include any additional user rules. At the bottom of the dialog box may be a "Submit" button, which the user may click when the applicable categories for the user rules have been made. After the "Submit" button is clicked, then the dialog box may then disappear.

Continuing the previous example, user rules were previously determined since the radiation oncology practice specializes in women's health. As such, the previously determined user rules are limited to women. Prior to uploading the data, the resident also set a few additional user rules. The resident clicked on the "User Rules" button located at the bottom of the main screen. A dialog box then appeared on the screen. The dialog box included a list of categories for the resident to select to include additional user rules for this specific patient. The list of categories included age group range, specific ethnicity and specific body part. To the left of each category was a box for the resident to select, if the resident selects that category. To the right of each category was a comment box for the resident to include more details related to the selected category. Since anaplastic astrocytoma is more common among people between the ages of 30 to 50, the resident decided to limit the images to that age range. As such, the resident selected the box to the left of age group, and then entered "30-50 ONLY" in the comment box located to the right of the age group category. The resident then clicked the "Submit" button located at the bottom of the dialog box. The dialog box then disappeared.

In the present embodiment, the dynamic image alteration program 110a, 110b may include default user rules. The default user rules are standard user rules that are included in every altered image. The default user rules may be removed by a system administrator and not a general user of the dynamic image alteration program 110a, 110b.

In the present embodiment, the dynamic image alteration program 110a, 110b may include recommended categories, or previously selected categories based on the rules previously selected by the user. Recommended categories or previously selected categories may be included in the list of categories. Each recommended or previously selected category may be designated with an asterisk.

In the present embodiment, the dynamic image alteration program 110a, 110b may prompt the user to provide additional clarification for a selected category. When the user clicks the "Submit" button located at the bottom of the dialog box, if the dynamic image alteration program 110a, 110b recommends further clarification to implement a specific user rule, then the user may be prompted (e.g., via another dialog box). The dialog box, for example, may reiterate the proposed user rule. At the bottom of the proposed user rule, there may be "Agree" or "Disagree" buttons which the user may select. If the user clicks the "Agree" button, then the proposed user rule may be implemented and the dialog box may disappear. If, however, the user clicks the "Disagree" button, then another dialog box may appear for the user to provide further clarification. The user may be prompted to provide further clarification to a user rule until the user clicks the "Agree" button for the proposed user rule. After multiple attempts to clarify a proposed user rule, the user may be prompted to cancel the user rule, or continue to provide further clarification until the user agrees with the proposed user rule.

If the dynamic image alteration program 110a, 110b determines that there are previously determined user rules at 204, then the dynamic image alteration program 110a, 110b applies the previously determined user rules at 206. The dynamic image alteration program 110a, 110b may apply these previously determined user rules to generate an altered image from the existing image received by the computerized medical image display program.

Continuing the previous example, the dynamic image alteration program 110a, 110b applied the previously determined user rules that limit the gender to women and the age group to persons between 30 and 50 years old.

Regardless if the dynamic image alteration program 110a, 110b determines there are no previously determined user rules at 204, or the dynamic image alteration program 110a, 110b applied the user rules at 206, the dynamic image alteration program 110a, 110b proceeds to determine if there is user input at 208. The dynamic image alteration program 110a, 110b may obtain the user input using the client computer 102 and prompt the user to provide user input to the dynamic image alteration program 110a, 110b. The user may be prompted (e.g., via a dialog box) to include user input. The dialog box, for example, may ask the user whether there is user input. Under the question, there may be "Yes" and "No" buttons for the user to select. If the user selects the "No" button for user input at 208, then the dynamic image alteration program 110a, 110b may proceed to generate an alteration of the existing image which will be described below at 212.

Continuing the previous example, after the previously determined user rules are applied to the received medical image, a dialog box then appeared on the screen. The dialog box asks the resident whether the resident has user input. Under the question, there are "Yes" or "No" buttons. The user selects the "Yes" button, and the dialog box then disappears. The resident will then be prompted to provide user input.

If, however, the dynamic image alteration program 110a, 110b determines that there is user input at 208, then the dynamic image alteration program 110a, 110b applies the user input at 210. A search and input process may be utilized to determine how the existing image with specific findings may be altered based on user input. The user may be prompted (e.g., via a dialog box) to provide user input in which the user may provide input (e.g., specific input) to alter (i.e., change the anatomical findings in a medical image to show another disease, remove a disease manifestation, or change a stage or severity of a disease manifestation) the existing image. The dialog box, for example, may include a list of proposed alterations for user input (e.g., progression or regression of one or multiple diseases (i.e., different severity and stages of one or multiple diseases), show a different disease state, show the manifestation of the disease in other organs or organ systems, depict a specific disease type, show a specific anatomical region, show an organ absent the disease, depict a portion of the existing image, change the size of the disease). To the left of each proposed alteration, there may be a box for the user to click to select that specific alteration. To the right of each proposed alteration, there may be a comment box for the user to provide additional details associated with the selected alteration. Under the list of proposed alterations, the dialog box may include a comment box for the user to provide additional alterations excluded in the list of proposed alterations. At the bottom of the dialog box, there is a "Submit" button which the user may click after the user has selected the specific alterations for the existing image. After the user clicks the "Submit" button, the dialog box may disappear.

Continuing the previous example, a dialog box to enter the user input appears on the screen after the dynamic image alteration program 110a, 110b applies the previously determined user rules. The dialog box includes a list of proposed alterations for the existing images. The resident selects three alterations from the list: (1) progression of the disease; (2) how the disease appears in a different state; and (3) manifestations of the disease in other organs or organ systems. As such, the resident selects the box located to the left of each proposed alteration and provides more details in the comment box located to the right of each proposed alteration. For the progression of the disease, the resident includes "indefinite" in the comment box. Therefore, the resident will view how the anaplastic astrocytoma progresses in women between the ages 30 and 50 for an unlimited period of time. The resident knows that anaplastic astrocytoma grade III may advance to glioblastoma grade IV (i.e., the most common and deadliest of the malignant primary brain tumors in adults). As such, the resident includes "glioblastoma grade IV" in the comment box to the right of the selected alteration on how the disease appears in a different state. The resident will view images of glioblastoma grade IV in women between the ages 30 and 50. Since anaplastic astrocytoma may spread to other parts of the brain or nervous system, and spreads, although rarely, to other organ systems outside of the central nervous system, the resident includes "left cerebral hemisphere, brain stem, spinal cord, and other organ systems outside of the central nervous system" in the comment box to the right of the selected alteration on manifestations of the disease in other organs or organ systems. The resident will view images of anaplastic astrocytoma in the left cerebral hemisphere, the brain stem, the spinal cord and other organ systems outside of the central nervous system in women between the ages of 30 and 50. After selecting the three proposed alterations of the existing images, the resident clicks the "Submit" button located on the bottom of the dialog box. The dialog box then disappears.

In the present embodiment, the user may select an automated test mode (i.e., automated test mode request). At the top of the dialog box displaying the list of proposed alterations for user input, there may be an "Automated Test Mode" button. If the user clicks the "Automated Test Mode" button, then the dynamic image alteration program 110a, 110b may automatically loop through different cases to test the user. The automated test mode may assist with the training of medical experts to identify and diagnose different diseases, especially rare diseases. In the present embodiment, the dynamic image alteration program 110a, 110b may continue in the automated test mode until the user achieves a certain result or threshold (e.g., satisfy a certain threshold of sensitivity and specificity diagnosing a target disease).

In the present embodiment, the dynamic image alteration program 110a, 110b may include alterations previously selected by the user (i.e., previously selected alterations). Previously selected alterations may be included in the list of alterations and may be designated with an asterisk to the right of the previously selected alteration.

In the present embodiment, the dynamic image alteration program 110a, 110b may include recommended alterations. Based on the patient's specific information, the dynamic image alteration program 110a, 110b may recommend alterations to the existing image. The recommended alterations may be designated with multiple asterisks to the right of the recommended alteration.

In the present embodiment, the dynamic image alteration program 110a, 110b may prompt the user to provide additional clarification for a selected alteration. When the user clicks the "Submit" button located at the bottom of the dialog box, the user may be prompted (e.g., via another dialog box) by the dynamic image alteration program 110a, 110b to provide further clarification to implement a specific alteration. The dialog box, for example, may reiterate the proposed alteration. At the bottom of the proposed alteration, there may be "Agree" or "Disagree" buttons which the user may select. If the user clicks the "Agree" button, then the proposed alteration may be implemented and the dialog box may disappear. If, however, the user clicks the "Disagree" button, then another dialog box may appear for the user to provide further clarification. The user may be prompted to provide further clarification to an alteration until the user clicks the "Agree" button for the proposed alteration. After multiple attempts to clarify a proposed alteration, the user may be prompted to cancel the proposed alteration, or continue to provide further clarification until the user agrees with the proposed alteration.

In the present embodiment, the dynamic image alteration program 110a, 110b may be integrated into a known medical imaging viewer to change the orientation of the altered image. Through the medical imaging viewer, the user may view the altered image and determine how the altered image may appear as another form of visual image (e.g., x-ray, radiograph, PET scan, CT scan).

In the present embodiment, the user may dynamically switch or shift between displays of various altered images to show the different stages or level of severity (i.e., progressions or regressions) of a medical condition.

In the present embodiment, the dynamic image alteration program 110a, 110b may determine the specific alterations for the images. While in the automated test mode, if the dynamic image alteration program 110a, 110b determines that the proposed alterations are closely related to a body type, possible diagnostic manifestation or medical condition (i.e., includes diagnosed or suspected medical condition), then the dynamic image alteration program 110a, 110b may generate altered images closely related to that medical condition or body type.

In the present embodiment, if the received data includes a specific medical finding (e.g., possible medical diagnosis), then the dynamic image alteration program 110a, 110b may generate altered images, while in the automated test mode, that are associated with that specific medical finding. The user may, however, override this function by changing the dynamic image alteration program 110a, 110b settings.

Regardless if the dynamic image alteration program 110a, 110b determined there was no user input at 208, or the dynamic image alteration program 110a, 110b applied the user input at 210, the dynamic image alteration program 110a, 110b proceeds to generate at least one alteration to the existing image (i.e., altered image) at 212. The dynamic image alteration program 110a, 110b may retrieve images from a known deep learning and image analysis engine with a medical knowledge base (e.g., PACS) based on the previously determined user rules at 206 and/or user input at 210. The dynamic image alteration program 110a, 110b may then utilize a known generative machine learning network to dynamically apply the changes displayed in the retrieved images from the PACS to the existing images specifically related to the data received on the specific patient to generate at least one altered image. The altered images may be anatomically altered, rather than an immaterial adjustment (e.g., change of window, level, color or filter), to create new anatomical findings. An adversarial neural network may be established for creating simulated altered images. The dynamic image alteration program 110a, 110b may then utilize a sample (i.e., at least one database image) from the medical knowledge base (e.g., database 114) of the deep learning and image analysis engine, as well as a sample from a known generator (e.g., a deep neural network). Both samples may be fed into a known discriminator (i.e., a convolutional neural network that is a parameterized function that attempts to distinguish between the samples from the real images and the altered images). Each altered and existing image may be presented to the user, or alternatively, the altered and existing images may be returned to the cloud storage service.

Continuing the previous example, the dynamic image alteration program 110a, 110b retrieves images from the medical knowledge base of the PACS, which are associated with the progression of anaplastic astrocytoma in women between the ages 30 and 50, glioblastoma grade IV in women between the ages 30 and 50, and the presence of anaplastic astrocytoma in the left cerebral hemisphere, the brain stem and the spinal cord in women between the ages of 30 and 50. From the medical knowledge base of the PACS, user rules, and user input, the dynamic image alteration program 110a, 110b retrieves 68 different images. The dynamic image alteration program 110a, 110b then utilizes the generative machine learning network to dynamically apply the changes thereby altering the 12 patient specific scans to show how anaplastic astrocytoma progresses, the presence of glioblastoma grade IV, and the presence or spread of anaplastic astrocytoma in the left cerebral hemisphere, the brain stem, the spinal cord and other organ systems outside of the central nervous system as it relates to this specific 39 year old female patient. The dynamic image alteration program 110a, 110b then generates 157 different altered images related to the specific patient based on the user input and rules. Of the 157 altered images generated by dynamic image alteration program 110a, 110b, 45 altered images show how the anaplastic astrocytoma progresses in the specific patient for the next five years, 80 altered images show the presence of glioblastoma grade IV at different stages of development in the specific patient, and 32 altered images show the presence of anaplastic astrocytoma in the left cerebral hemisphere, brain stem and spinal cord, as well as in the rare cases, the spread of anaplastic astrocytoma to the skeletal system (i.e., bones) and respiratory system (i.e., lungs).

In the present embodiment, the dynamic image alteration program 110a, 110b may retrieve images from the medical knowledge base with similar demographic information as the patient from the received medical data. The retrieved images may be utilized to generate altered images. If, however, the user prefers to change these settings, then, the settings may be modified by a system administrator. Additionally, the retrieved and altered images may be utilized by the dynamic image alteration program 110a, 110b while the dynamic image alteration program 110a, 110b is in automated test mode.

In the present embodiment, the altered images may be presented to the user. The dynamic image alteration program 110a, 110b may present the altered image on a screen for the user to review. The altered image may be proximally displayed to the user (e.g., side-by-side or in a stack). Each altered image may include a brief description under the image indicating the alteration and user rules utilized to generate the altered image, and other important details related to the altered image (e.g., time-period, type of scan, orientation). For example, the altered images are displayed on the screen for the user to proximally review. The user sequentially reviews each of the altered images where the images related to the progression of the specific disease are organized from the least to most progressed stage or severity, and a brief description is included with each altered image explaining the time-period, and alteration and/or user rules applied to generate the altered image.

In the present embodiment, two or more altered images may be organized based on type of alteration implemented to generate the image, and time-period or interval associated with the altered image (i.e., default settings). Additionally, two or more altered images may be proximally displayed to the user (e.g., side-by-side or in a stack). If, however, the user prefers to change the default settings, then the settings may be modified by a system administrator.

Then, at 214, the dynamic image alteration program 110a, 110b determines if the user has additional user input. The dynamic image alteration program 110a, 110b may obtain the additional user input using the client computer 102 and prompt the user to provide additional user input to the dynamic image alteration program 110a, 110b. After the altered image is displayed, the user may be prompted (e.g., via a dialog box) to include additional alterations that the user failed to previously include. The dialog box, for example, may ask the user whether there is any additional user input not previously included by user. Under the question, there may be "Yes" and "No" buttons for the user to select.

If the dynamic image alteration program 110a, 110b determines that the user has no additional user input at 214, then the dynamic image alteration program 110a, 110b may conclude. The user may then continue to review the altered image, and any existing or comparative images generated for the specific patient.

Continuing the previous example, after the 157 altered images are generated and displayed for the user, a dialog box appears asking whether the user has any additional user input. The resident clicked the "No" button under the question in the dialog box. The dialog box then disappears and the resident continues to review the altered images.

If the dynamic image alteration program 110a, 110b determines that the user has additional user input at 214, then the dynamic image alteration program 110a, 110b may return to 210 to apply user input. The dynamic image alteration program 110a, 110b may utilize the additional user input to generate secondary altered images.

Continuing the previous example, if the resident selected the "Yes" button in the dialog box to provide additional user input, then the dynamic image alteration program 110a, 110b returns to 210 to apply the user input.

In the present embodiment, the user may compare altered and existing images in the dynamic image alteration program 110a, 110b. At the top of the altered image, there may be a "Compare" button for the user to compare multiple images. If the user clicks the "Compare" button, the user may be prompted (e.g., via a dialog box) to compare one or multiple generated images (i.e., existing images received from the patient's data, or altered images based on one or more user rules or input) with the altered image. The dialog box, for example, may include two buttons, "Existing Image(s)" or "Altered Image(s)." If the user selects the "Existing Image(s)" button, then the user may select to compare the altered image with at least one existing image received from the patient's data. Another dialog box may appear in which the existing images received from the patient's data may be included for the user to review and select at least one existing image to review and compare with the altered image. If, however, the user selects "Altered Image," then the user may compare the altered image with another altered image based on at least one user rule or alteration selected at 214 (i.e., "comparable image"). Another dialog box, for example, may appear in which the user rules and alterations are listed, and the user may select at least one user rule or alteration to exclude from the comparable image. Once the user selected at least one user rule or alteration, the user may click the "Submit" button located at the bottom of the dialog box. Then the dialog box may disappear. The user may utilize the dynamic image alteration program 110a, 110b for a proximal comparison (e.g., side-by-side or in a stack) of the comparable or existing image with the altered image.

The present embodiment may include alternate means (e.g., audio command, direct screen editing of the existing image) for the user provide user rules or input. The user may indicate the alternate means, for example, by selecting the "Command" button located at the bottom of the screen. Alternatively, the means of providing user rules or input may depend on the computerized medical image display program utilized by the user.

The present embodiment may include an option for the user to save all or some of the images generated (e.g., altered, comparable or existing images). The saved images may be saved onto computer-readable tangible storage devices, portable computer-readable tangible storage devices, or a user's computer 102 for research and training purposes, or review by the user at a later time. The saved images may be indexed to limit access to certain users based on the role or rights of the user. The rights of the user may be previously set by the user and may be approved by the system administrator. Additionally, the altered images may be indexed based on how each image is altered. According to at least one embodiment, the saved images may be stored as a reference image in a medical knowledge base.

In the present embodiment, the dynamic image alteration program 110a, 110b and the deep learning and image analysis engine with a medical knowledge base may utilize natural language processing (NLP) to process user rules and input for retrieving and altering the existing image.

The present embodiment may be utilized to alter non-static images (e.g., video or movies) to train the user to rapidly respond to images in various domains (e.g., pilots, fire fighters, police officers, physicians, drivers).

It may be appreciated that FIG. 2 provides only an illustration of one embodiment and does not imply any limitations with regard to how different embodiments may be implemented. Many modifications to the depicted embodiment(s) may be made based on design and implementation requirements.

Figure 3:
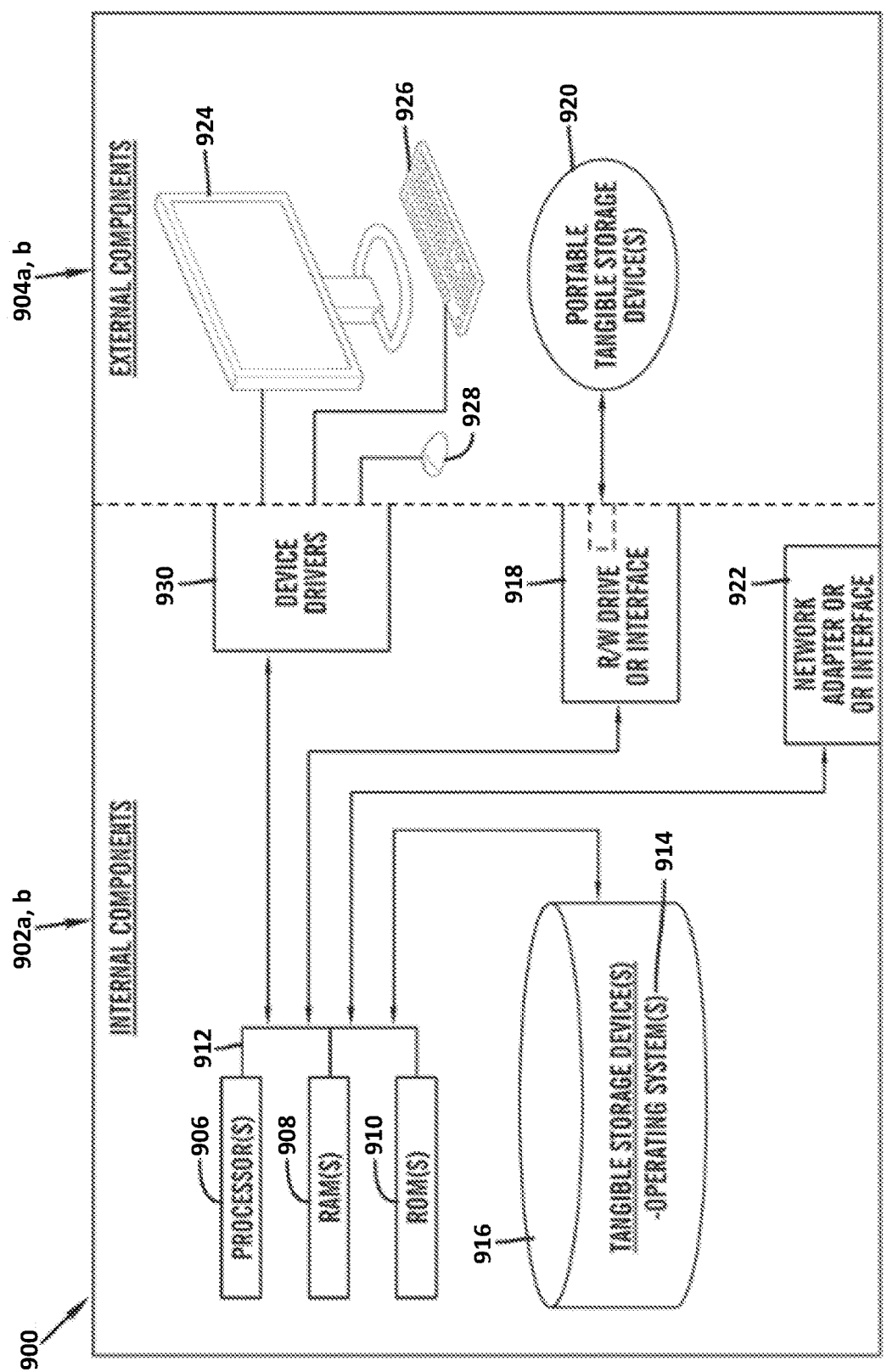
FIG. 3 is a block diagram of internal and external components of computers and servers depicted in FIG. 1 according to at least one embodiment.

FIG. 3 is a block diagram 900 of internal and external components of computers depicted in FIG. 1 in accordance with an illustrative embodiment of the present invention. It should be appreciated that FIG. 3 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902 a, b and external components 904 a, b illustrated in FIG. 3. Each of the sets of internal components 902 a, b includes one or more processors 906, one or more computer-readable RAMs 908 and one or more computer-readable ROMs 910 on one or more buses 912, and one or more operating systems 914 and one or more computer-readable tangible storage devices 916. The one or more operating systems 914, the software program 108 and the dynamic image alteration program 110a in client computer 102, and the dynamic image alteration program 110b in network server 112, may be stored on one or more computer-readable tangible storage devices 916 for execution by one or more processors 906 via one or more RAMs 908 (which typically include cache memory). In the embodiment illustrated in FIG. 3, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902 a, b also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the dynamic image alteration program 110a and 110b can be stored on one or more of the respective portable computer-readable tangible storage devices 920, read via the respective R/W drive or interface 918 and loaded into the respective hard drive 916.

Each set of internal components 902 a, b may also include network adapters (or switch port cards) or interfaces 922 such as a TCP/IP adapter cards, wireless Wi-Fi interface cards, or 3G or 4G wireless interface cards or other wired or wireless communication links. The software program 108 and the dynamic image alteration program 110a in client computer 102 and the dynamic image alteration program 110b in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the dynamic image alteration program 110a in client computer 102 and the dynamic image alteration program 110b in network server computer 112 are loaded into the respective hard drive 916. The network may comprise copper wires, optical fibers, wireless transmission, routers, firewalls, switches, gateway computers and/or edge servers.

Each of the sets of external components 904 a, b can include a computer display monitor 924, a keyboard 926, and a computer mouse 928. External components 904 a, b can also include touch screens, virtual keyboards, touch pads, pointing devices, and other human interface devices. Each of the sets of internal components 902 a, b also includes device drivers 930 to interface to computer display monitor 924, keyboard 926, and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., fl networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Analytics as a Service (AaaS): the capability provided to the consumer is to use web-based or cloud-based networks (i.e., infrastructure) to access an analytics platform. Analytics platforms may include access to analytics software resources or may include access to relevant databases, corpora, servers, operating systems or storage. The consumer does not manage or control the underlying web-based or cloud-based infrastructure including databases, corpora, servers, operating systems or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
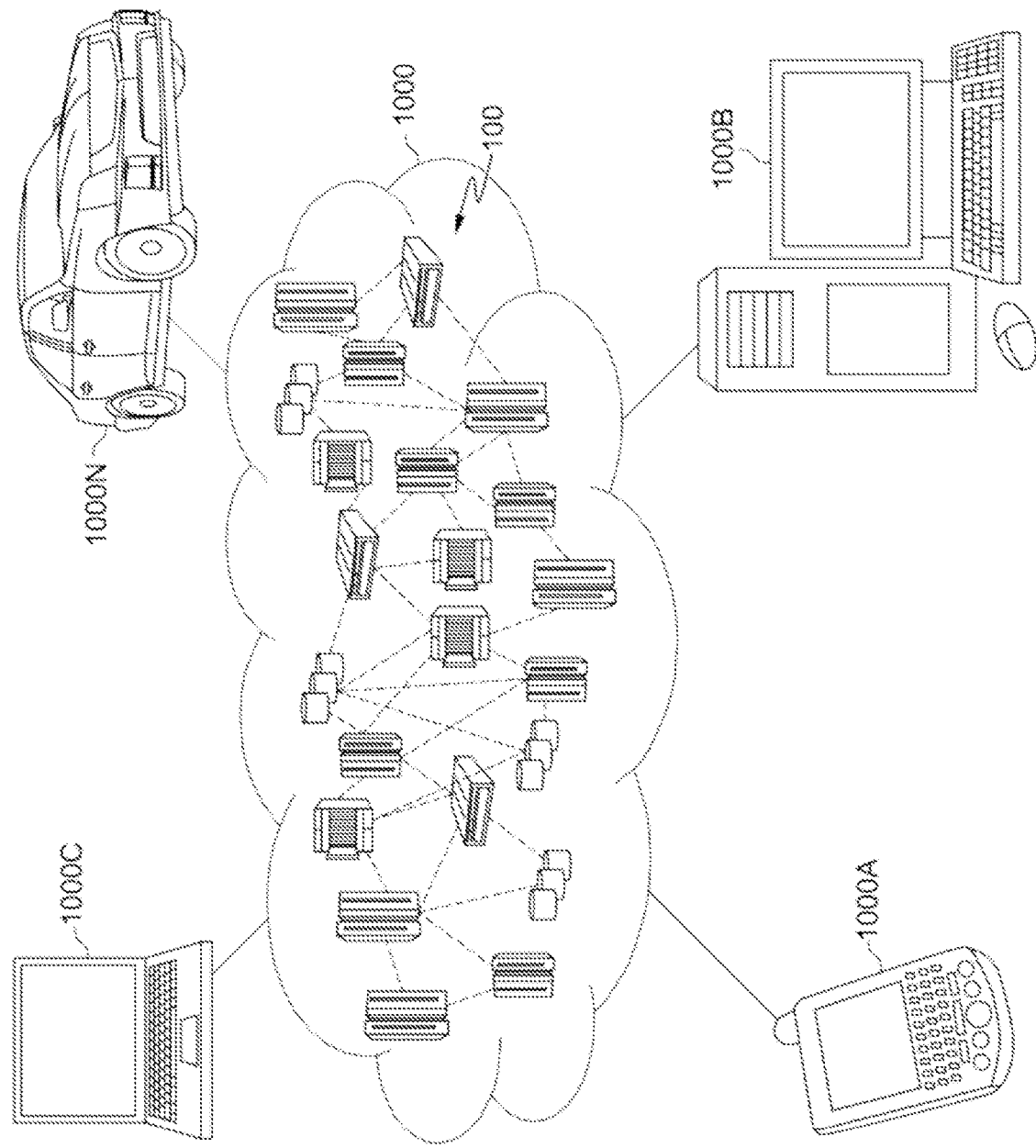
FIG. 4 is a block diagram of an illustrative cloud computing environment including the computer system depicted in FIG. 1, in accordance with an embodiment of the present disclosure.

Referring now to FIG. 4, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 4 are intended to be illustrative only and that computing nodes 100 and cloud computing environment 1000 can communicate with any type of computerized device over any type of network and/or network addressable connection (e.g., using a web browser).

Figure 5:
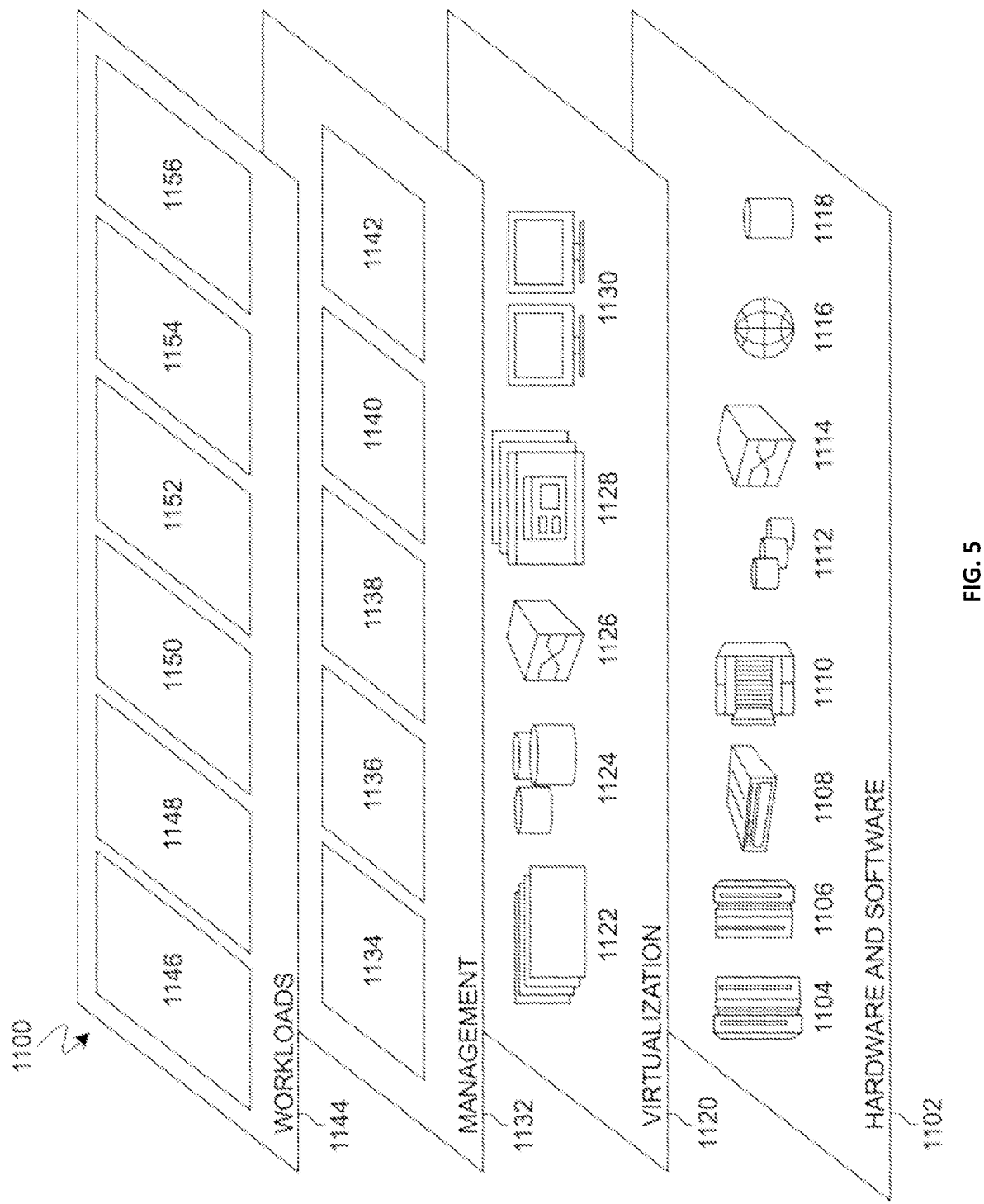
FIG. 5 is a block diagram of functional layers of the illustrative cloud computing environment of FIG. 4, in accordance with an embodiment of the present disclosure.

Referring now to FIG. 5, a set of functional abstraction layers 1100 provided by cloud computing environment 1000 is shown. It should be understood in advance that the components, layers, and functions shown in FIG. 5 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and dynamic image alteration 1156. A dynamic image alteration program 110a, 110b provides a way to dynamically alter an image based on user rules and actions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for dynamically altering at least one image, comprising:
   receiving a plurality of data, wherein the received plurality of data includes at least one existing medical image;
   determining that one or more user instructions for the received existing image were received;
   implementing the one or more user instructions on the received existing medical image; and
   altering the received existing medical image based on the one or more implemented user instructions and a medical knowledge base,
      wherein in response to determining at least one medical condition in connection with the received plurality of data, determining a plurality of progressions and a plurality of regressions based on the determined medical condition,
      wherein the existing medical image is determined based on the determined plurality of progressions and determined plurality of regressions to the determined medical condition,
      wherein the user dynamically switches the generated plurality of progressions and the generated plurality of regressions of the received existing medical image.

2. The method of claim 1, further comprising:
   presenting the altered one or more images to the user, wherein the altered one or more images are proximally presented to the user.

3. The method of claim 1, wherein determining that one or more user instructions for the received existing image were received, further comprises:
   determining that one or more configurable rules for the received existing image were received;
   implementing the determined one or more configurable rules on the received existing medical image; and
   altering the received existing medical image based on the implemented one or more configurable rules and the medical knowledge base.

4. The method of claim 1, wherein determining that one or more user instructions for the received existing image were received, further comprises:
   determining that one or more user input for the received existing image were received;
   implementing the determined one or more user input on the received existing medical image; and
   altering the received existing medical image based on the implemented one or more user input and the medical knowledge base.

5. The method of claim 1, further comprising:
   receiving at least one specific disease type selected by the user; and
   altering the at least one existing medical image, wherein the altered at least one existing medical image depicts the received specific disease type.

6. The method of claim 1, further comprising:
   receiving an automated test mode request from the user;
   determining at least one possible diagnoses based on the received existing medical image and the medical knowledge base;
   generating a plurality of computer-generated images based on the received existing medical image by utilizing the medical knowledge base, wherein the generated plurality of computer-generated images includes the determined at least one possible diagnoses; and
   presenting, to the user, the generated plurality of computer-generated images, wherein the generated plurality of computer-generated images assists with the identification of a plurality of specific medical findings.

7. The method of claim 1, further comprising:
   receiving an automated test mode request by the user;
   generating a plurality of computer-generated images based on the implemented one or more configurable rules on the received existing medical image; and
   presenting, to the user, the generated plurality of computer-generated images, wherein the generated plurality of computer-generated images assists to identify a plurality of specific medical findings, and wherein the generated plurality of computer-generated images continue until a threshold is exceeded.

8. The method of claim 1, further comprising:
receiving at least one specific anatomical region selected by the user;
determining at least one medical condition in connection with the received plurality of data; and
altering at least one existing medical image, wherein the altered at least one existing medical image depicts the selected at least one specific anatomical region and the determined medical condition.

9. The method of claim 1, further comprising:
determining at least one medical condition associated with the received plurality of data;
retrieving, from the medical knowledge base, at least one reference image in connection with the determined medical condition; and
altering the received existing medical image based on the retrieved at least one reference image.

10. A computer system for dynamically altering at least one image, comprising:
one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:
receiving a plurality of data, wherein the received plurality of data includes at least one existing medical image;
determining that one or more user instructions for the received existing image were received;
implementing the one or more user instructions on the received existing medical image; and
altering the received existing medical image based on the one or more implemented user instructions and a medical knowledge base,
wherein in response to determining at least one medical condition in connection with the received plurality of data, determining a plurality of progressions and a plurality of regressions based on the determined medical condition,
wherein the existing medical image is determined based on the determined plurality of progressions and determined plurality of regressions to the determined medical condition,
wherein the user dynamically switches the generated plurality of progressions and the generated plurality of regressions of the received existing medical image.

11. The computer system of claim 10, further comprising:
presenting the altered one or more images to the user, wherein the altered one or more images are proximally presented to the user.

12. The computer system of claim 10, wherein determining that one or more user instructions for the received existing image were received, further comprises:
determining that one or more configurable rules for the received existing image were received;
implementing the determined one or more configurable rules on the received existing medical image; and
altering the received existing medical image based on the implemented one or more configurable rules and the medical knowledge base.

13. The computer system of claim 10, wherein determining that one or more user instructions for the received existing image were received, further comprises:
determining that one or more user input for the received existing image were received;
implementing the determined one or more user input on the received existing medical image; and
altering the received existing medical image based on the implemented one or more user input and the medical knowledge base.

14. The computer system of claim 10, further comprising:
receiving at least one specific disease type selected by the user; and
altering the at least one existing medical image, wherein the altered at least one existing medical image depicts the received specific disease type.

15. The computer system of claim 10, further comprising:
receiving an automated test mode request from the user;
determining at least one possible diagnoses based on the received existing medical image and the medical knowledge base;
generating a plurality of computer-generated images based on the received existing medical image by utilizing the medical knowledge base, wherein the generated plurality of computer-generated images includes the determined at least one possible diagnoses; and
presenting, to the user, the generated plurality of computer-generated images, wherein the generated plurality of computer-generated images assists with the identification of a plurality of specific medical findings.

16. The computer system of claim 10, further comprising:
receiving an automated test mode request by the user;
generating a plurality of computer-generated images based on the implemented one or more configurable rules on the received existing medical image; and
presenting, to the user, the generated plurality of computer-generated images, wherein the generated plurality of computer-generated images assists to identify a plurality of specific medical findings, and wherein the generated plurality of computer-generated images continue until a threshold is exceeded.

17. A computer program product for dynamically altering at least one image, comprising:
one or more computer-readable storage media and program instructions stored on at least one of the one or more tangible storage media, the program instructions executable by a processor to cause the processor to perform a method comprising:
receiving a plurality of data, wherein the received plurality of data includes at least one existing medical image;
determining that one or more user instructions for the received existing image were received;
implementing the one or more user instructions on the received existing medical image; and
altering the received existing medical image based on the one or more implemented user instructions and a medical knowledge base,
wherein in response to determining at least one medical condition in connection with the received plurality of data, determining a plurality of progressions and a plurality of regressions based on the determined medical condition,
wherein the existing medical image is determined based on the determined plurality of progressions and determined plurality of regressions to the determined medical condition,
wherein the user dynamically switches the generated plurality of progressions and the generated plurality of regressions of the received existing medical image.

18. The computer program product of claim 17, wherein determining that one or more user instructions for the received existing image were received, further comprises:
- determining that one or more configurable rules for the received existing image were received;
- implementing the determined one or more configurable rules on the received existing medical image; and
- altering the received existing medical image based on the implemented one or more configurable rules and the medical knowledge base.

19. The computer program product of claim 17, wherein determining that one or more user instructions for the received existing image were received, further comprises:
- determining that one or more user input for the received existing image were received;
- implementing the determined one or more user input on the received existing medical image; and
- altering the received existing medical image based on the implemented one or more user input and the medical knowledge base.

* * * * *